United States Patent [19]

Vander Zwan

[11] 4,100,159

[45] Jul. 11, 1978

[54] PROCESS FOR PREPARATION OF 9-(2,6-DIHALOBENZYL)ADENINES

[75] Inventor: Michael C. Vander Zwan, Maple Glen, Pa.

[73] Assignee: Merck & Co., Inc., Rahway, N.J.

[21] Appl. No.: 766,326

[22] Filed: Feb. 7, 1977

[51] Int. Cl.² .......................................... C07D 473/34
[52] U.S. Cl. .................................... 544/277; 424/253
[58] Field of Search ................................ 260/252, 254

[56] References Cited

U.S. PATENT DOCUMENTS

| | | | |
|---|---|---|---|
| 3,846,426 | 11/1974 | Lira et al. | 260/252 |
| 3,953,597 | 4/1976 | Lira et al. | 260/252 |
| 3,992,432 | 11/1976 | Napier et al. | 260/465.1 |

OTHER PUBLICATIONS

Durst et al., J. Org. Chem., 39, 3271 (1974).
Landini et al., Synthesis, 389 (1976).
Gokel et al., Aldrichimica, Acta, 9, 3 (1976).
Jones, Aldrichimica, Acta, 9, 35 (1976).
Dehmlow, Chemtech, 210–218 (1975).
Starks, J. Amer. Chem. Soc., 93:1 (1971).

*Primary Examiner*—Nicholas S. Rizzo
*Attorney, Agent, or Firm*—Walter Patton

[57] ABSTRACT

9-(2,6-Dihalobenzyl)adenines are prepared by allowing 2,6-dihalobenzyl halides to react with a salt of adenine in a solid-liquid or liquid-liquid two phase system in the presence of an onium salt phase transfer catalyst. The resulting compounds have anticoccidial activity and are useful in controlling cecal and/or intestinal coccidiosis when administered in minor quantities to animals, in particular to poultry usually in admixture with animal sustenance.

4 Claims, No Drawings

PROCESS FOR PREPARATION OF 9-(2,6-DIHALOBENZYL)ADENINES

BACKGROUND OF THE INVENTION

This invention relates to a novel process for preparing 9-(2,6-dihalobenzyl)adenines. Said adenines are described in U.S. Pat. No. 3,846,426 as being useful in the treatment and prevention of coccidoisis.

Coccidiosis is a widespread poultry disease which is produced by infections of protozoa of the genus Eimeria which causes severe disorders in the intestines and ceca of poultry. Some of the most significant of these species are E. tenella, E. acervulina, E. necatrix, E. brunetti and E. maxima. This disease is generally spread by the birds picking up the infectious organism in droppings on contaminated litter or ground, or by way of food drinking water. The disease is manifested by hemorrhage, accumulation of blood in the ceca, passage of blood in the droppings, weakness and digestive disturbances. The disease often terminates in the death of the animal, but the fowl which survive severe infections have had their market value substantially reduced as a result of the infection. Coccidiosis is, therefore, a disease of great economic importance and extensive work has been done to find new and improved methods for controlling and treating coccidial infections in poultry.

Prior art base catalyzed alkylations of adenine were carried out in aqueous solvents or aqueous protic organic solvents. These reactions were homogenous and rapid but suffered from the disadvantage that mixtures of 3-isomer and 9-isomer were obtained which contain a high proportion of 3-isomer. The 3-isomer and 9-isomer can be exemplified by the following structural formulas:

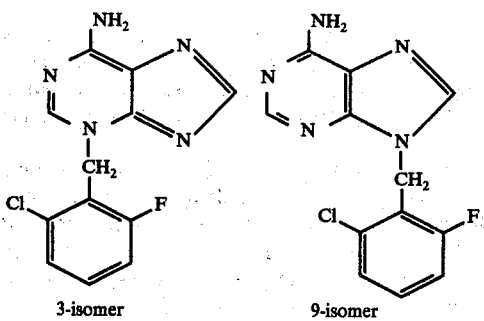

3-isomer      9-isomer

Base catalyzed alkylations of adenine carried out in aprotic solvents such as dimethylformamide and dimethylsulfoxide provide a higher ratio of 9-isomer with respect to 3-isomer but suffer from the disadvantage that these solvents are costly. The isolation of the product is also made more difficult. The reaction mixture has to be quenched in water and the product, collected by filtration, has to be repeatedly washed to remove solvent. This results in a reduction of yield.

Solvents such as dimethylformamide and dimethylsulfoxide do not dissolve the alkali metal or alkaline earth metal salts of adenine to any great extent, however, the fraction which does dissolve is highly dissociated and results in a "naked adenine anion" or a "loose ion pair" which is rapidly alkylated. According to the process of the present invention, the salt of adenine is transported from a solid phase or an aqueous phase by the action of a "phase transfer catalyst" into an aprotic organic solvent phase in which phase alkylation takes place. The advantage of the present invention is that alkylations can be carried out in aprotic solvents in which the alkali metal or alkaline metal salts are otherwise insoluble or in which, if solution occurs, very little dissociation occurs and alkylation is slow due to lack of "naked adenine anions".

The present invention differs from the process of the prior art in that a "phase transfer catalyst", either an ammonium or phosphonium salt, is present which enhances the rate of alkylation and enables the reaction to be carried out in an aprotic solvent in which alkali and alkaline earth metal salts of adenine are not generally soluble. Carrying out the alkylation in aprotic solvents yields predominately the 9-isomer. "Phase transfer catalysts" also allow one to carry out the alkylation at room temperature and for short reaction periods to obtain a product containing a high ratio of 9-isomer with respect to 3-isomer. For example, alkylations carried out in acetone are accelerated as much as five to ten-fold without affecting selectivity when carried out in the presence of a "phase transfer catalyst".

The role of the "phase transfer catalysts" is presumed to be to convert the alkali or alkaline earth metal salts of adenine to tetraalkyl ammonium or tetraalkyl of phosphonium salts. The resulting ammonium and phosphonium salts of adenine are more soluble and readily dissociated in the organic phase in which phase alkylation occurs. Accordingly, the ammonium or phosphonium salts catalyze the transport of adenine from either an aqueous phase or a solid phase into an organic phase. Hence, these salts are herein referred to as "phase transfer catalysts".

SUMMARY OF THE INVENTION

An object of this invention is to provide an improved novel method for preparing a mixture of isomers of (2,6-dihalobenzyl)adenine in which the 9-(2,6-dihalobenzyl)adenine predominates. According to the process of the present invention the purine derivatives are prepared by alkylating a salt of adenine with a 2,6-dihalobenzyl halide in a solid-liquid two phase system wherein the solid phase comprises the salt of adenine and the liquid phase comprises a solution of the alkylating agent and an onium salt in an organic solvent; or a liquid-liquid two phase system wherein one liquid phase comprises an aqueous solution of adenine salt and a second liquid phase comprising the alkylating agent and the onium salt. The onium salt, such as an ammonium or phosphonium salt is used as a catalyst to transport the salt of adenine from the solid phase into the liquid organic phase or from the aqueous liquid phase to the organic liquid phase where alkylation of adenine takes place. The process is generally referred to as "phase transfer catalysis" and the onium salt referred to as a "phase transfer catalyst".

DESCRIPTION OF THE PREFERRED EMBODIMENTS

The compounds prepared by the novel process of the present invention are represented by the following structural formula:

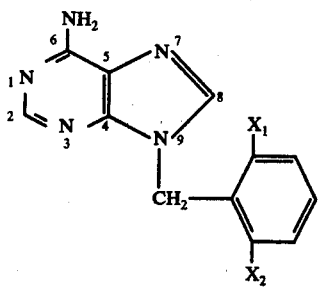

wherein $X_1$ and $X_2$ are independently halogen, i.e., fluorine, chlorine, bromine or iodine. Specific examples of compounds represented by the foregoing structural formula are 9-(2,6-dichlorobenzyl)adenine and 9-(2-chloro-6-fluorobenzyl)adenine.

According to the improved process of the present invention an alkali or alkaline earth metal salt of adenine is alkylated with 2,6-dihalobenzyl halide to give a mixture of isomers of (2,6-dihalobenzyl)adenine in which at least about 70% by weight is 9-(2,6-dihalobenzyl)adenine wherein the improvement comprises carrying out the alkylation in a solid-liquid or liquid-liquid two phase system wherein, (a) the solid-liquid two phase system comprises a solid phase comprising an alkali or alkaline earth metal salt of adenine and a liquid phase comprising a solution of 2,6-dihalobenzyl halide and an onium salt "phase transfer catalyst" having the structure:

$(R)_3^{\oplus}N\ R_1\ Z^{\ominus}$ or $(R_1)_3P^{\oplus}R\ Z^{\ominus}$ wherein R is alkyl having 4 to 18 carbon atoms, $R_1$ is alkyl having 1 to 8 carbon atoms and $Z^{\ominus}$ is an anion selected from the group consisting of chlorine, bromine and iodine in an aprotic water miscible or water immiscible organic solvent wherein the water miscible solvent contains from 0 to about 5 moles of water per mole of adenine salt, (b) the liquid-liquid two phase system comprises one liquid phase comprising an aqueous solution of an alkali or alkaline earth metal salt of adenine and a second liquid phase comprising a solution of 2,6-dihalobenzyl halide and an onium salt phase transfer catalyst having the structure:

$(R)_3N^{\oplus}R_1\ Z^{\ominus}$ or $(R_1)_3P^{\oplus}R\ Z^{\ominus}$ wherein R, $R_1$ and $Z^{\ominus}$ are as defined above in an aprotic water immiscible organic solvent.

The "phase transfer catalyst" consists of onium salts containing alkyl groups attached to nitrogen or phosphorus atoms. Any alkyl ammonium or phosphonium salts may be employed in the process of the present invention provided that the alkyl groups are sufficiently large enough to solubilize the adenine salt in the selected organic phase but not so large that emulsions occur. Suitable alkyl groups are those containing from 1 to 18 carbon atoms.

Suitable solvent systems for the process of the present invention are aprotic solvents that are inert, i.e., non-reactive with the components of the reaction mixture under the reaction conditions that are maintained. Aprotic solvents are preferred for the reason that a high ratio of 9-isomer with respect to 3-isomer is obtained. In the case wherein the reaction is carried out in a solid-liquid two phase system the aprotic solvent may be either water miscible or immiscible. It is not critical to maintain the water miscible solvents in an anhydrous condition, however, excessive amounts of water tend to result in a higher proportion of 3-isomer. In the case wherein a liquid-liquid two phase is employed, the aprotic organic solvent is limited to those not miscible with water. The quantity of water in the aqueous phase is not critical.

The alkali or alkaline earth metal salt of adenine has the structure:

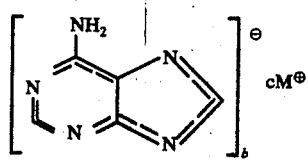

wherein $M^+$ is an alkali or alkaline earth metal cation; $b$ and $c$ are integers such that the negative charge of $b$ moles of anion are neutralized by $c$ moles of cation, $M^{\oplus}$, the salt is suspended in an aprotic organic solvent or dissolved in an aqueous solution. To this is added a solution containing the alkylating agent having the structure:

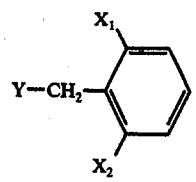

wherein $X_1$ and $X_2$ are as defined above and Y is a leaving group and an onium salt "phase transfer catalyst" in an aprotic solvent. The resulting heterogeneous reaction mixture is stirred rapidly until completion of the reaction.

In the preferred process of the present invention the suspension comprising the alkali or alkaline earth metal salt of adenine in the selected solvent is treated with 2,6-disbustituted toluene substituted at the α-position with a suitable leaving group. Leaving groups useful in the process of the present invention are selected from the group consisting of halogen, dimethylsulfonium halide and tosyl. The preferred leaving group is halogen. The substituted toluene is added in an equimolar amount with respect to adenine or in a slight excess.

According to the process of the present invention, adenine is suspended in a suitable aprotic solvent. To this is added an equivalent amount of base. Preferred bases are those having a $pK_b$ greater than 10.5 so that the adenine is substantially completely converted to its anion. Examples of suitable bases include carbonates, e.g., alkali metal carbonates such as sodium carbonate and potassium carbonate, hydroxides, e.g., alkali metal hydroxides such as sodium hydroxide, potassium hydroxide and lithium hydroxide, tetraalkyl ammonium hydroxide and alcoholates, e.g., potassium ethoxide, sodium ethoxide. In general, suitable bases include all those that have a sufficient basicity to generate the adenine anion in the solvent system used.

In the process of the present invention, the adenine salt may be prepared in situ by the addition of an equivalent amount of base or the adenine salt may conveniently be prepared by dissolving the adenine in an aqueous solution containing an equivalent amount of strong base evaporating the water and using the residue containing the adenine salt hydrate in the alkylation.

A preferred aspect of the present invention is the improved process for alkylating an alkali earth metal salt of adenine with 2-chloro-6-fluorobenzyl halide or 2,6-dichlorobenzyl halide and producing a mixture of isomers of (2-chloro-6-fluorobenzyl)adenine or (2,6-dichlorobenzyl)adenine in which at least about 70% by weight is 9-(2-chloro-6-fluorobenzyl)adenine or 9-(2,6-dichlorobenzyl)adenine wherein the improvement comprises carrying out the alkylation in a solid-liquid or liquid-liquid two phase system. The solid-liquid two phase system comprises a solid phase of an alkali earth metal salt of adenine and a liquid phase of a solution of 2-chloro-6-fluorobenzyl halide or 2,6-dichlorobenzyl halide and a quaternary ammonium salt phase transfer catalyst having the structure:

wherein R is alkyl having 4 to 18 carbon atoms, $R_1$ is alkyl having 1 to 8 carbon atoms and $Z^\ominus$ is an anion selected from the group consisting of chlorine, bromine and iodine in an aprotic water miscible solvent selected from the group consisting of acetone, acetonitrile and hexamethylphosphoramide wherein the water miscible solvent may contain from 0 to 5 moles of water per mole of adenine salt and still produce the desired ratio of the 9-isomer. The reaction may also be carried out in a water immiscible organic solvent selected from the group consisting of hexane, benzene, toluene, methylene chloride, chloroform and petroleum ether.

When the reaction is carried out in a liquid-liquid two phase system, one liquid phase is an aqueous solution of an alkali earth metal salt of adenine and the second liquid phase is a solution of 2-chloro-6-fluorobenzyl halide or 2,6-dichlorobenzyl halide and a quaternary ammonium salt phase transfer catalyst having the structure:

wherein R, $R_1$ and $Z^\ominus$ are as defined above in an aprotic water immiscible organic solvent selected from the group consisting of hexane, benzene, toluene, methylene chloride, chloroform and petroleum ether.

A still further preferred aspect of the present invention is the improved process for alkylating sodium adeninate with 2-chloro-6-fluorobenzyl chloride and producing a mixture of isomers of (2-chloro-6-fluorobenzyl)adenine in which at least about 70% by weight is 9-(2-chloro-6-fluorobenzyl)adenine wherein the improvement comprises carrying out the alkylation in a solid-liquid or liquid-liquid two phase system wherein, in the solid-liquid reaction system the solid phase comprises sodium adeninate and the liquid phase comprises an acetone solution of 2-chloro-6-fluorobenzyl chloride and a quaternary ammonium salt phase transfer catalyst having the structure:

wherein R is a mixture of normal alkanes containing 8 to 12 carbon atoms. This mixture of tetraalkylammonium salts in which R is primarily caprylyl ($C_8$) is known as Aliquat 336 (manufactured by General Mills, Inc., Chemical Division, 4620 West 77th Street, Minneapolis, Minnesota). The reaction mixture does not have to be anhydrous, it may contain from 0 to about 5 moles of water per mole of sodium adeninate and still yield the desired proportion of the 9-isomer.

When the reaction is carried out in a liquid-liquid two phase system one liquid phase comprises an aqueous solution of an alkali earth metal salt of adenine and a second liquid phase comprises a hexane solution of 2-chloro-6-fluorobenzyl chloride and a quaternary ammonium salt phase transfer catalyst having the structure:

wherein R is alkyl having 8 to 12 carbon atoms and $Z^\ominus$ is an anion selected from the group consisting of chlorine, bromine and iodine.

In the process of the present invention, the relative proportions of the adenine and alkylating agent may vary over a relatively wide range. The reactants may be used in stoichiometric amounts i.e, equal moles of the reactants may be used or an excess e.g, a 2 to 10% or even greater molar excess of the alkylating agent may be used. A preferred excess is about 2 mole %. It is preferred that the phase transfer catalyst be used in an amount from about 1 mole % to 10 mole % relative to adenine. The amount of the solvent used may also vary over a wide range. The solvent is used in a quantity sufficient to permit stirring the heterogeneous reaction mixture to allow the reaction to proceed at a reasonable rate and facilitate isolation of the reaction product. In most cases a 5 to 15 weight % solution of adenine salt in solvent is suitable for carrying out the reaction.

The components of the reaction mixture are combined in the reaction medium in any convenient manner and in any order. As illustrative of a suitable manner of combining the components of the reaction mixture, the adenine is added to a solution of the base in the reaction medium, after which the substituted toluene is added, either neat or in a suitable solvent and finally the "phase transfer catalyst" is added. Other methods of combining the reactants and catalyst will be obvious to one skilled in the art but it is preferred that they be combined so that the anion of the adenine forms no later than the time when the substituted toluene is added and most preferably prior to such time. The "phase transfer catalyst" is most preferably added last.

The reaction time and temperature conditions are not unduly critical. The time of the reaction will, however, decrease as the reaction temperature increases. The reaction will most conveniently be conducted between a temperature in the range of from about room temperature to about 150° C. However, it is preferred to carry out the reaction at the reflux temperature of the selected solvent. In the case of the solvent, hexamethylphosphoramide, temperatures in excess of 155° C. are to be avoided as the selectivity of the alkylation decreases with excessively high temperatures. The reaction may be carried out from 1 hour to 24 hours but in most cases alkylation is complete after 4 to 6 hours.

After the reactants are thus contacted with each other in the presence of the "phase transfer catalyst" in the reaction medium, the product of the reaction, i.e., the 9-(dihalobenzyl)adenine, either as a pure compound or along with the other isomer that forms, (e.g., the 3-isomer) will either remain entirely in solution or precipitate on standing, depending upon the quantity of solvent utilized. Upon completion of the reaction, the reaction mixture may be cooled, e.g., to a temperature of about room temperature to precipitate a solid product or to precipitate a further quantity of this product. The product is then isolated in the usual manner, such as by filtration, and, if desired, purified by conventional methods such as washing with ethanol or water and recrystallizing from a suitable solvent such as acetic acid, aqueous acetic acid, dimethylformamide or dimethylsulfoxide. Swishing the product with dilute nitric acid or tetrafluoroboric acid (HBF$_4$) also results in purification.

The weight % of 9-isomer and 3-isomer in the product is determined by high pressure liquid chromatography (L.C.) and U.V., respectively. The weight % of 9-isomer is determined by a high pressure liquid chromatography assay (L.C.) using a Zurbax-Silica column eluted with CHCl$_3$:MeOH (95:5) and measuring the absorbance of each component at 254 nm, 9-benzyladenine was used an an internal standard (accurate to ±0.3%). The weight % of the 3-isomer is determined by U.V. assay. The sample is assayed in 0.1N methanolic base at 310 nm, the 3-isomer has an ε of 2300 at this wave-length and the 9-isomer does not absorb (accurate to ±0.1%).

The following non-limiting Examples will serve to further illustrate the instant invention.

EXAMPLE 1

Process for Alkylating Adenine with α,2-Dichloro-6-fluorotoluene in the Presence of Aliquat 336 in Hexane-Water (Liquid-liquid Heterogeneous Reaction Mixture)

A 1-liter three-necked round bottom flask equipped with a thermometer, condenser, nitrogen inlet and an overhead mechanical stirrer was charged sequentially with 40 ml. of water, 8.0 g. of sodium hydroxide (0.20 mole) and, after the sodium hydroxide dissolved, 27.60 g. of adenine (98% pure, 0.20 mole). After the adenine was dissolved, a solution of 39.95 g. of α,2-dichloro-6-fluorotoluene (91.5% pure by G.C. assay, 0.20 mole plus 2%) and 5.04 g. of Aliquat 336 (0.01 mole, 5 mole %) in 300 ml. of hexane was added. (No reaction takes place if the "phase transfer catalyst" is omitted). The mixture was stirred at reflux for 6 hours, cooled to room temperature and the solids collected by filtration. The solids were washed twice with 100 ml. of water and dried in vacuo (100° C. overnight) to give 52.32 g. of 2-chloro-6-fluorobenzylated adenines (94%). U.V. (N/10 HCl) λ max = 264, E% = 535; L.C. wt. % 9-isomer = 69.9; U.V. wt. % 3-isomer = 25.0.

Purification of Crude 2-Chloro-6-Fluorobenzylated Adenines

Thirty g. of the above crude material was added to 60 ml. of hot acetic acid (65° C.). The temperature was raised to 100° C. at which point all the material dissolved. The hot acetic acid solution was filtered through a preheated glass fritted funnel and the filtrate was added dropwise over a 10 minute period to 240 ml. of well-stirred water at 95° C. (addition of water to the acetic acid solution gives the acetate salt of the product which is a cotton-like material). When the solution cooled to 37° C. the bulk of the product precipitated. The product was collected by filtration, washed once with 25 ml. of acetic acid-water (1:4), twice with 25 ml. of water and dried in vacuo (95° C. for 6 hours) to give 20.83 g. of 9-(2-chloro-6-fluorobenzyl)adenine (69.5%). U.V. wt. % 3-isomer = 3.0; L.C. wt. % 9-isomer = 89.

EXAMPLE 2

Process for Alkylating Adenine with α,2-Dichloro-6-fluorotoluene in the Presence of Aliquat 336 in Acetone (Solid-liquid Reaction Mixture)

A 250 ml. round bottom flask was sequentially charged with 100 ml. of acetone, 6.95 g. of adenine 97% pure, 50 mmole) and 4.0 g. of sodium hydroxide solution (assay 50%, 50 mmole) and the suspension refluxed for one and one-half hours. The suspension was charged with a solution of 9.8 g. of α,2-dichloro-6-fluorotoluene (91.4% pure, 50 mmole) and 1.25 g. of Aliquat 336 (2.5 mmole, 5 mole %) in 10 ml. of acetone and refluxed, with rapid stirring, for 6 hours. (In the absence of the "phase transfer catalyst" the reaction is about 5x slower.) The reaction mixture was cooled to room temperature and the solids collected by filtration. The solids were washed twice with 15 ml. of acetone and then swished with 50 ml. of 0.1N sodium hydroxide solution for 15 minutes (this removes any unreacted adenine and the NaCl formed during the alkylation). The solids were collected by filtration, washed twice with 20 ml. of water and dried in vacuo (100° C. for 4.5 hours) to give 13.12 g. of 2-chloro-6-fluorobenzylated adenines (94.4%). U.V. (N/10 HCl)λmax = 262, E% = 534; L.C. wt. % 9-isomer = 77.4; U.V. wt. % 3-isomer = 20.4.

Purification

Ten g. of the above material was added to 18 ml. of hot glacial acetic acid (~60° C.). The mixture was heated to 110° C. (solution occurred between 60° and 90° C.), filtered and the filtrate added to 80 ml. of hot water (95° C.) over a 5-minute period with rapid stirring (2 more ml. of acetic acid were used for rinses). When the temperature dropped to 37° C. the suspended solids were collected by filtration, washed once with 10 ml. of 4:1 H$_2$O:HOAc and twice with 15 ml. of water. Vacuum oven drying (100° C. for 6 hours) gave 7.64 g. of 9-(2-chloro-6-fluorobenzyl)adenine, 76.4%. U.V. (N/10 HCl) λ max = 260, E% 570; DSC = 0.5 mole % impurity, m.p. (uncor) = 244.5–246° C.; tlc on silica gel in CHCl$_3$: MeOH (10:1) showed one minor impurity at R$_f$ = 0.57 and a main spot at R$_f$ = 0.86.

EXAMPLE 3

Process for Alkylating Sodium Adeninate Hydrate with α,2-Dichloro-6-fluorotoluene in the Presence of Aliquat 336 in Hexamethylphosphoramide (Solid-liquid Reaction Mixture)

Step 1:

Sodium adeninate hydrate was conveniently prepared by dissolving one mole of adenine in 400 ml. of 2.5M sodium hydroxide (1.0 mole). The solution was concentrated on a rotary evaporator in vacuo at steam bath temperature until it became supersaturated. The solution was poured into a glass pan and after the sodium adeninate crystallized, the material was dried in vacuo overnight at 75° C. The dried material was ground into a free flowing powder; KF = 8.3%; Eq. Wt. (HClO$_4$) = 85.4 (MW = 170.8) (eq. wt. titrations with HCl gave values of 172–173).

Step 2: Alkylation

A 100 ml. flask was charged with 50 ml. of hexamethylphosphoramide (HMPA) (no special drying was done) and 8.55 g. (50 mmole) of sodium adeninate hydrate (prepared by the process set forth in Example 3, Step 1). After all the sodium adeninate was uniformly suspended, 9.9 g. of α,2-dichloro-6-fluorotoluene (92.3% pure, 50 mmole plus 2%) was added over a 10–15 minute period. The reaction was stirred overnight (4 hours was adequate for complete conversion) and then slowly poured (3 minutes) into 100 ml. of water with rapid stirring (pH = 7.9 after about 5 minutes). Sodium hydroxide solution, 0.6 g. (assay 50%, 7.5 mole), was added to the suspension to ensure removal of unreacted adenine. After stirring for 15 minutes, the suspended solids were collected by filtration, washed twice with 25 ml. of water and dried in vacuo (4 hours, 75° C.) to give 13.29 g. of 2-chloro-6-fluorobenzylated adenines (95.8%). U.V. wt. % 3-isomer = 11.7; L.C. wt. % 9-isomer = 84.8.

Step 3: Purification

Ten g. of the above material was dissolved in 14 ml. of 95° C. acetic acid. The solution was filtered hot and the filtrate added dropwise within a few minutes to 80 ml. of 95° C. water with rapid stirring (2 additional ml. of hot acetic acid were used to rinse all remaining material into the hot water). After cooling to 37° C., the suspended solids were collected by filtration, washed once with 10 ml. of acetic acid-water (1:5), twice with 10 ml. of water and dried in vacuo (overnight, 75° C.) to give 8.45 g. of 9-(2-chloro-6-fluorobenzyl)adenine (84.5%). Tlc on silicagel in CHCl$_3$:MeOH (10:1) indicated a single spot; m.p. 243–245° C.; DSC = 0.8 mole % impurity; U.V. (N/10 HCl) λ max = 259, E% = 562; U.V. wt. % 3-isomer = < 2.

EXAMPLE 4

Process for Alkylating Sodium Adeninate Hydrate with α,2-Dichloro-6-fluorotoluene in the Presence of Aliquat 336 in Acetone (Solid-liquid Reaction Mixture)

A 250 ml. round bottom flask was sequentially charged with 100 ml. of acetone, and 8.54 g. of sodium adeninate hydrate (50 mmole, prepared by the process set forth in Example 3, Step 1). The suspension was charged with a solution of 9.8 g. of α,2-dichloro-6-fluorotoluene (91.4% pure, 50 mmole) and 1.25 g. of Aliquat 336 (2.5 mmole, 5 mole %) in 10 ml. of acetone and refluxed with rapid stirring for 6 hours. The reaction mixture was cooled to room temperature and the solids collected by filtration, washed twice with 15 ml. of acetone and then swished with 50 ml. of 0.1N sodium hydroxide solution for 15 minutes (this removes any unreacted adenine and the NaCl formed during the alkylation). The solids were collected by filtration, washed twice with 20 ml. of water and dried in vacuo (100° C., 4.5 hours) to give 13.2 g. of 2-chloro-6-fluorobenzylated adenines (95%). U.V. (N/10 HCl)λ max = 262, E% = 534; L.C. wt. % 9-isomer = 83; U.V. wt. % 3-isomer = 16.

EXAMPLE 5

Process for Alkylating Potassium Adeninate Hydrate with α,2-Dichloro-6-fluorotoluene in the Presence of Aliquat 336 in Acetone (Solid-liquid Reaction Mixture)

The process was carried out as set forth in Example 4, with the exception that the sodium adeninate was replaced by an equivalent amount of potassium adeninate. The potassium adeninate was prepared by the process set forth in Example 3, Step 1 with the exception that an equivalent amount of potassium hydroxide was substituted for the sodium hydroxide.

The yield of 2-chloro-6-fluorobenzylated adenines was 94%. L.C. wt. % 9-isomer = 82; U.V. wt. % 3-isomer = 18.

EXAMPLE 6

Process for Alkylating Sodium Adeninate Hydrate with α-(Y)-2-chloro-6-fluorotoluene in the Presence of Aliquat 336 in Acetone (Solid-liquid Reaction Mixture)

The process was carried out as set forth in Example 4, with the exception that the α,2-dichloro-6-fluorotoluene was replaced by an equivalent amount of α-(Y)-2-chloro-6-fluorotoluene wherein Y has the values set forth in Table I below:

TABLE I

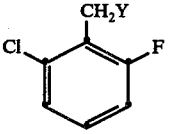

| | Yield of 2-Chloro-6-fluorobenzylated adenines | Ratio of 9-isomer to 3-isomer* |
|---|---|---|
| 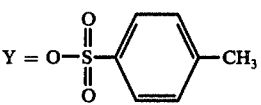 tosyl | 85% | 2:1 |
| Y = I | 85% | 7:3 |
| Y = S$^{\oplus}$(CH$_3$)$_2$Cl$^{\ominus}$ | 31% | 3:1 |
| Y = Br | 85% | 4:1 |

*In some cases small amounts of up to 10% of other products, presumably other isomers were obtained (1-isomer and 7-isomer).

EXAMPLE 7

Process for Alkylating Sodium Adeninate Hydrate with α,2,6-Trichlorotoluene in the Presence of Aliquat 336 in Acetone (Solid-liquid Reaction Mixture)

A 250 ml. round bottom flask was sequentially charged with 100 ml. of acetone and 8.54 g. of sodium adeninate hydrate (50 mmole, prepared by the process set forth in Example 3, Step 1). The suspension was charged with a solution of 10 g. of α,2,6-trichlorotoluene (98% pure, 50 mmole) and 1.25 g. of Aliquat 336 (2.5 mmole, 5 mole %) in 10 ml. of acetone and refluxed, with rapid stirring, for 6 hours. The reaction mixture was cooled to room temperature and the solids collected by filtration, wahsed twxe with 15 ml. of acetone and then swished with 50 ml. of 0.1N sodium hydroxide solution for 15 minutes (this removes any unreacted adenine and the NaCl formed during the alkylation). The solids were collected by filtration, washed twice with 20 ml. of water and dried in vacuo (100° C., 4.5 hours) to give 13.8 g. of 2,6-dichlorobenzylated adenines (94%). U.V. (N/10 HCl) λ max = 262, E% = 494; L.C. wt. % 9-isomer = 81; U.V. wt. % 3-isomer = 17.

EXAMPLE 8

Process for Alkylating Sodium Adeninate Hydrate with α,2,6-Trichlorotoluene in the Presence of Aliquat 336 in Toluene (Solid-liquid Reaction Mixture)

A 250 ml. round bottom flask was sequentially charged with 100 ml. of toluene and 8.54 g. of sodium adeninate hydrate (50 mmole, prepared by the process set forth in Example 3, Step 1). The suspension was charged with a solution of 10 g. of α,2,6-trichlorotoluene (98% pure, 50 mmole) and 1.25 g. of Aliquat 336 (2.5 mmole, 5 mole %) in 10 ml. of toluene and refluxed with rapid stirring for 6 hours. The reaction mixture was cooled to room temperature and the solids collected by filtration, washed twice with 15 ml. of toluene and then swished with 50 ml. of 0.1N sodium hydroxide solution for 15 minutes (this removes any unreacted adenine and the NaCl formed during the alkylation). The solids were collected by filtration, washed twice with 20 ml. of water and dried in vacuo (100° C., 4.5 hours) to give 10.2 g. of 2,6-dichlorobenzylated adenines (76%). U.V. (N/10 HCl) λ max = 262, E% = 498; L.C. wt. % 9-isomer = 80; U.V. wt. % 3-isomer = 20.

Although this invention has been described in relation to specific embodiments, it will be apparent that obvious modifications may be made by one skilled in the art without departing from the intended scope thereof as defined by the appended claims.

What is claimed is:

1. An improved process for alkylating an alkali or alkaline earth metal salt of adenine with 2,6-dihalobenzyl halide and producing a mixture of isomers of (2,6-dihalobenzyl)adenine in which at least about 70% by weight is 9-(2,6-dihalobenzyl)adenine wherein the improvement comprises carrying out the alkylation in a rapidly stirred solid-liquid or liquid-liquid two phase system wherein,
   (a) the solid-liquid two phase system comprises a solid phase comprising an alkali or alkaline earth metal salt of adenine and a liquid phase comprising a solution of 2,6-dihalobenzyl halide and an onium salt phase transfer catalyst having the structure:

 or

wherein R is alkyl having 4 to 18 carbon atoms, $R_1$ is alkyl having 1 to 8 carbon atoms and $Z^\ominus$ is an anion selected from the group consisting of chlorine, bromine and iodine in an aprotic water miscible or water immiscible organic solvent wherein the water miscible solvent contains from 0 to about 5 moles of water per mole of adenine salt,
   (b) the liquid-liquid two phase system comprises one liquid phase comprising an aqueous solution of an alkali or alkaline earth metal salt of adenine and a second liquid phase comprising a solution of 2,6-dihalobenzyl halide and an onium salt phase transfer catalyst having the structure:

 or

wherein R, $R_1$ and $Z^\ominus$ are as defined above in an aprotic water immiscible organic solvent; wherein the phase transfer catalyst is used in an amount from about 1 mole % to about 10 mole % relative to adenine and the alkylation is carried out at a temperature range of room temperature to 150° C. from about 1 hour to about 24 hours.

2. An improved process according to claim 1 for alkylating an alkali earth metal salt of adenine with 2-chloro-6-fluorobenzyl halide or 2,6-dichlorobenzyl halide and producing a mixture of isomers of (2-chloro-6-fluorobenzyl)adenine or (2,6-dichlorobenzyl)adenine in which at least about 70% by weight is 9-(2-chloro-6-fluorobenzyl)adenine or 9-(2,6-dichlorobenzyl)adenine wherein the improvement comprises carrying out the alkylation in a solid-liquid or liquid-liquid two phase system wherein,
   (a) the solid-liquid two phase system comprises a solid phase comprising an alkali earth metal salt of adenine and a liquid phase comprising a solution of 2-chloro-6-fluorobenzyl halide or 2,6-dichlorobenzyl halide and a quaternary ammonium salt phase transfer catalyst having the structure:

wherein R is alkyl having 4 to 18 carbon atoms, $R_1$ is alkyl having 1 to 8 carbon atoms and $Z^\ominus$ is an anion selected from the group consisting of chlorine, bromine and iodine in an aprotic water miscible solvent selected from the group consisting of acetone, acetonitrile and hexamethylphosphoramide wherein the water miscible solvent contains from 0 to 5 moles of water per mole of adenine salt, or a water immiscible organic solvent selected from the group consisting of hexane, benzene, toluene, methylene chloride, chloroform and petroleum ether,
   (b) the liquid-liquid two phase system comprises one liquid phase comprising an aqueous solution of an alkali earth metal salt of adenine and a second liquid phase comprising a solution of 2-chloro-6-fluorobenzyl halide or 2,6-dichlorobenzyl halide and a quaternary ammonium salt phase transfer catalyst having the structure:

wherein R, $R_1$ and $Z^\ominus$ are as defined above in an aprotic water immiscible organic solvent selected from the group consisting of hexane, benzene, toluene, methylene chloride, chloroform and petroleum ether.

3. An improved process according to claim 2 for alkylating sodium adeninate with 2-chloro-6-fluorobenzyl chloride and producing a mixture of isomers of (2-chloro-6-fluorobenzyl)adenine in which at least about 70% by weight is 9-(2-chloro-6-fluorobenzyl)adenine wherein the improvement comprises carrying out the alkylation in a solid-liquid two phase system wherein, the solid phase comprises sodium adeninate and the liquid phase comprises a solution of 2-chloro-6-fluorobenzyl chloride and a quaternary ammonium salt phase transfer catalyst having the structure:

wherein R is normal alkyl containing 8 to 12 carbon atoms in acetone containing from 0 to about 5 moles of water per mole of sodium adeninate.

4. An improved process according to claim 2 for alkylating sodium adeninate with 2-chloro-6-fluorobenzyl chloride and producing a mixture of isomers of (2-chloro-6-fluorobenzyl)adenine in which at least about 70% by weight is 9-(2-chloro-6-fluorobenzyl)adenine wherein the improvement comprises carrying out the alkylation in a liquid-liquid two phase system wherein, one liquid phase comprises an aqueous solution of an alkali earth metal salt of adenine and a second liquid phase comprises a solution of 2-chloro-6-fluorobenzyl chloride and a quaternary ammonium salt phase transfer catalyst having the structure:

wherein R is alkyl having 8 to 12 carbon atoms and $Z^\ominus$ is an anion selected from the group consisting of chlorine, bromine and iodine in hexane.

* * * * *

UNITED STATES PATENT OFFICE
CERTIFICATE OF CORRECTION

Patent No. 4,100,159                    Dated July 11, 1978

Inventor(s) Michael C. Vander Zwan

It is certified that error appears in the above-identified patent and that said Letters Patent are hereby corrected as shown below:

At Column 4, structure after line 12, please correct to read as follows:

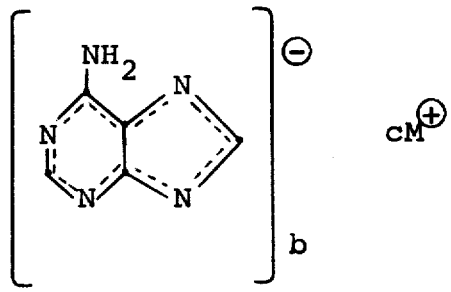

[SEAL]

Attest:

Attesting Officer

Signed and Sealed this

Fourth Day of March 1980

SIDNEY A. DIAMOND

Commissioner of Patents and Trademarks